(12) United States Patent
Akteries et al.

(10) Patent No.: US 6,521,792 B2
(45) Date of Patent: Feb. 18, 2003

(54) PROCESS FOR SEPARATING THE DIASTEREOMERIC BASES OF 2-[(DIMETHYLAMINO)METHYL]-1-(3-METHOXYPHENYL)-CYLOHEXANOL

(75) Inventors: Bernhard Akteries, Aachen (DE); Michael Finkam, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 10/024,590

(22) Filed: Dec. 21, 2001

(65) Prior Publication Data

US 2002/0091287 A1 Jul. 11, 2002

Related U.S. Application Data

(63) Continuation of application No. PCT/EP99/04325, filed on Jun. 22, 1999.

(51) Int. Cl.[7] ............................................. C07C 209/88
(52) U.S. Cl. ........................ 564/424; 564/307; 564/425
(58) Field of Search ................................ 564/307, 424, 564/425

(56) References Cited

U.S. PATENT DOCUMENTS

| 3,830,934 | A | * | 8/1974 | Flick et al. | 424/330 |
|---|---|---|---|---|---|
| 5,414,129 | A | * | 5/1995 | Cherkez et al. | 564/425 |
| 5,672,755 | A | * | 9/1997 | Lerman et al. | 564/425 |
| 5,874,620 | A | * | 2/1999 | Lerman et al. | 564/443 |
| 5,877,351 | A | * | 3/1999 | Anderson | 564/425 |

FOREIGN PATENT DOCUMENTS

| DE | 43 30 240 A1 | * | 3/1994 | C07C/217/74 |
|---|---|---|---|---|
| WO | WO 99/03820 | * | 1/1999 | C07C/213/10 |

* cited by examiner

*Primary Examiner*—Brian Davis
(74) *Attorney, Agent, or Firm*—Crowell & Moring, LLP

(57) ABSTRACT

A method for separating the diastereomer bases of 2-[(dimethylamino)methyl]-1-(3-methoxyphenyl)-cyclohexanol in which the separation of the diastereomer bases takes place through formation of a base hydrate.

6 Claims, No Drawings

PROCESS FOR SEPARATING THE DIASTEREOMERIC BASES OF 2-[(DIMETHYLAMINO)METHYL]-1-(3-METHOXYPHENYL)-CYLOHEXANOL

CROSS REFERENCE TO RELATED APPLICATIONS

This application is a continuation of international patent application no. PCT/EP99/04325, filed Jun. 22, 1999, designating the United States of America, the entire disclosure of which is incorporated herein by reference.

BACKGROUND OF THE INVENTION

This invention relates to a process for the purification and separation of the diastereomers of 2[(dimethylamino)methyl]-1-(3-methoxyphenyl)cyclohexanol.

This compound and the salts thereof are of pharmaceutical interest. Tramadol hydrochloride, CA no. 36282-47-0 (±)-trans-2-[(dimethylamino)methyl]-1-(3-methoxyphenyl) cyclohexanol hydrochloride has long been commercially available as a highly effective analgesic.

The above designation of the cis/trans isomers is not in accordance with IUPAC nomenclature. Compound CA no. 36282-47-0 is accordingly hereinafter designated the cis isomer or cis-tramadol in accordance with IUPAC nomenclature and taken to encompass the racemic mixture of (1R,2R)- and (1S,2S)-2-[(dimethylamino)methyl]-1-(3-methoxyphenyl)cyclohexanol, while the racemic mixture of (1R,2S)- and (1S,2R)-2-[(dimethylamino)methyl]-1-(3-methoxyphenyl)cyclohexanol is designated the trans isomer or trans-tramadol.

Known purification and separation processes, e.g., U.S. Pat. No. 3,830,934 and DE-OS 4 330 240, for the aforementioned tramadol hydrochloride are based on the reaction of the diastereoisomeric base mixture with mineral acids and subsequent fractional crystallization from organic solvents. The disadvantage of this procedure is that it gives rise to two or more fractions which require further processing, so greatly reducing economic viability. Moreover, since concentrated mineral acids are sometimes used, this procedure inevitably gives rise to decomposition products due to the acid lability of the tertiary alcohol function. Furthermore, separation of the cis/trans isomers may only be achieved by means of the above-stated process if the isomer ratio of the base mixture to be separated is greater than 75:25 cis:trans.

WO 99/03820 describes a process for the production of pure cis-tramadol hydrochloride, in which a monohydrate of the corresponding cis-tramadol base is obtained from the Grignard bases by addition of water and is separated.

In all previously known processes, the trans:trans isomer ratio of the diastereomeric base mixtures to be separated is 80:20 and above. For example, according to DE-OS 4 330 240 or U.S. Pat. No. 5,414,129, the ratio is 86:14.

However, there is also interest in separating the desired cis isomer from mixtures which contain the diastereomeric bases in an unfavorable isomer ratio, in order, for example, to be able to work up Grignard reaction mixtures obtained from deviant reaction conditions or also mother liquors. Mother liquors arising from a first precipitation of the desired isomer still contain the diastereomeric bases in a cis:trans isomer ratio of approx. 50:50.

SUMMARY OF THE INVENTION

The object of the invention is accordingly to provide a process which, without primary salt formation, permits separation of the diastereomers from a diastereomeric base mixture of 2-[(dimethylamino)methyl]1-(3-methoxyphenyl) cyclohexanol over a wide isomer ratio range.

It has surprisingly been found that diastereomer separation with 2-[(dimethylamino)methyl]-1-(3-methoxyphenyl) cyclohexanol advantageously proceeds by formation of a base hydrate by adding water or preferably organic solvent or solvent mixture and water to a diastereomeric base mixture of this compound with a cis:trans isomer ratio of below 80:20.

The invention accordingly provides a process for the separation of the diastereomeric bases of 2[(dimethylamino) methyl]-1-(3-methoxyphenyl)cyclohexanol by treatment with water in at least stoichiometric quantities for complete conversion of the bases and subsequent separation of the precipitated hydrate of the cis diastereomer, which process is characterised in that a base mixture with a cis:trans isomer ratio of below 80:20, preferably of 60:40–75:25, is used.

DETAILED DESCRIPTION OF PREFERRED EMBODIMENTS

When separating contaminated diastereomeric base mixtures, said mixtures are preferably dissolved in a water-miscible organic solvent or solvent mixture before the reaction with water, wherein solvents from the group of alcohols, ketones, esters, ethers, low molecular weight polyalcohols or aromatic hydrocarbons are used. The organic solvent or solvent mixture is here preferably used in a volume ratio to water of 10:2–10:5.

The water-miscible organic solvents used are preferably $C_{1-8}$ alcohols, $C_{3-8}$ ketones, $C_{2-8}$ esters, aliphatic, aromatic, open-chain and cyclic $C_{4-8}$ ethers, $C_{2-6}$ polyalcohols or $C_{6-9}$ aromatics.

The separated hydrate crystals of the cis diastereomer are finally washed with a mixture of the organic solvent and water in a volume ratio of 10:2–10:5 and then dried.

The water is used in at least stoichiometric quantities for complete conversion of the bases. Moreover, the water and also the solvent or solvent mixture may be used with the diastereomeric base mixture in a wide range of mixing ratios.

Separation of the diastereomers may proceed over a wide temperature range, provided that it is ensured that the reaction mixture does not freeze out at low temperatures. At higher temperatures, the temperature of the reaction mixture is preferably maintained below the melting point of the base hydrate.

The process according to the invention is characterised in that, under the described conditions, the diastereomeric base mixture forms a hydrate and this hydrate, namely the cis diastereomer, preferably precipitates, so enabling easy separation of the diastereomers.

In comparison with heretofore described procedures, the process offers the advantages that diastereomer separation may proceed without salt formation (for example via the hydrochloride), that unwanted decomposition products are simply and effectively avoided by the formation of the base hydrate and that subsequent salt formation with numerous acids is possible directly via the base stage. Above all, however, the process makes it possible to separate diastereomeric base mixtures, the cis:trans isomer ratio of which deviates greatly from that conventionally arising after the Grignard reaction. In particular, the process is suitable for working up mother liquors.

EXAMPLES

Example 1

50 g of a diastereomeric base mixture of (±)-cis/trans-2-[(dimethylamino)methyl]-1-(3-methoxyphenyl)

cyclohexanol (cis:trans isomer ratio=75:25) were dissolved in 100 ml of acetone. 20 ml of water were then added and the reaction mixture stirred at 20° C. Crystallisation began after approx. 30 minutes. The suspension was stirred for a further 90 minutes. The crystals were separated from the mother liquor using a filter, were washed twice with an acetone/water mixture (volume ratio 10:2) and suction filtered dry. The hydrate of the cis diastereomer was obtained at a yield of 67% and a purity of greater than 95%. The isomer ratio in the crystal fraction was 98% cis isomer to 2% trans isomer.

Example 2

50 g of a diastereomeric base mixture of (±)-cis/trans-2-[(dimethylamino)methyl]-1-(3-methoxyphenyl)cyclohexanol (cis:trans isomer ratio=75:25) were dissolved in 100 ml of isopropanol. 50 ml of water were then added and the reaction mixture stirred at 45° C. Crystallisation began after approx. 20 minutes. The suspension was stirred for a further 90 minutes. The crystals were separated from the mother liquor using a filter, were washed twice with an isopropanol/water mixture (volume ratio 10:5) and suction filtered dry. The hydrate of the cis diastereomer was obtained at a yield of 64% and a purity of greater than 95%. The isomer ratio in the crystal fraction was 97% cis isomer to 3% trans isomer.

Example 3

50 g of a diastereomeric base mixture of (±)-cis/trans-2-[(dimethylamino)methyl]-1-(3-methoxyphenyl)cyclohexanol (cis:trans isomer ratio=75:25) were dissolved in 50 ml of tetrahydrofuran (THF). 25 ml of water were then added and the reaction mixture stirred at 0° C. Crystallisation began overnight. The suspension was stirred for a further 90 minutes. The crystals were separated from the mother liquor using a filter, were washed twice with an THF/water mixture (volume ratio 10:5) and suction filtered dry. The hydrate of the cis diastereomer was obtained at a yield of 66% and a purity of greater than 95%. The isomer ratio in the crystal fraction was 98% cis isomer to 2% trans isomer.

Example 4

100 g of a diastereomeric base mixture of (±)-cis/trans-2-[(dimethylamino)methyl]-1-(3-methoxyphenyl)cyclohexanol (cis:trans isomer ratio=75:25) were exposed to atmospheric humidity. After 3 days, a crystalline mass was obtained, which, after washing three times with cold ethanol/water, gave rise to the hydrate of the cis diastereomer at a yield of 45% and a purity of 95%. The isomer ratio in the crystal fraction was 98.1% cis isomer to 1.9% trans isomer.

Example 5

Conversion of a base hydrate obtained according to the invention into a salt: 20 g of the moist crystallisate obtained according to Example 1 were dissolved in 40 ml of isopropanol and stirred together with 36% hydrochloric acid until the measured pH value of the solution fell below 3. The solvent was then stripped out and the product recrystallised from isopropanol. Tramadol hydrochloride was obtained.

Example 6

50 g of a diastereomeric base mixture of (±)-cis/trans-2-[(dimethylamino)methyl]-1-(3-methoxyphenyl)cyclohexanol (cis:trans isomer ratio=63:37) were dissolved in 100 ml of acetone. 20 ml of water were then added and the reaction mixture stirred at 20° C. Crystallisation began after approx. 30 minutes. The suspension was stirred for a further 90 minutes. The crystals were separated from the mother liquor using a filter, were washed twice with an acetone/water mixture (volume ratio 10:2) and suction filtered dry. The hydrate of the cis diastereomer was obtained at a yield of 36% and a purity of greater than 95%. The isomer ratio in the crystal fraction was 97% cis isomer to 3% trans isomer.

Example 7

20 g of a diastereomeric base mixture of (±)-cis/trans-2-[(dimethylamino)methyl]-1-(3-methoxyphenyl)cyclohexanol (cis:trans isomer ratio=75:25) were dissolved in 20 g of ethanol at 22° C. and combined with 20 vol. % of water. The solution was cooled to 6° C. and left to stand for 6 hours. The resultant crystals were removed by suction filtration and washed twice with 10 ml portions of ethanol/water. After drying, the hydrate of the cis diastereomer is obtained at a yield of 34% and a purity of greater than 95%. The isomer ratio in the crystal fraction was 98.8% cis isomer to 1.2% trans isomer.

Example 8

20 g of a diastereomeric base mixture of (±)-cis/trans-2-[(dimethylamino)methyl]-1-(3-methoxyphenyl)cyclohexanol (cis:trans isomer ratio=75:25) were dissolved in 20 g of ethanol at 22° C. and combined with 33 vol. % of water. The solution was cooled to 6° C. and left to stand for 6 hours. The resultant crystals were removed by suction filtration and washed twice with 10 ml portions of ethanol/water. After drying, the hydrate of the cis diastereomer is obtained at a yield of 43% and a purity of greater than 95%. The isomer ratio in the crystal fraction was 99.4% cis isomer to 0.6% trans isomer.

Example 9

20 g of a diastereomeric base mixture of (±)-cis/trans-2-[(dimethylamino)methyl]-1-(3-methoxyphenyl)cyclohexanol (cis:trans isomer ratio=75:25) were dissolved in 20 g of ethanol at 22° C. and combined with 40 vol. % of water. The solution was cooled to 6° C. and left to stand for 6 hours. The resultant crystals were removed by suction filtration and washed twice with 10 ml portions of ethanol/water. After drying, the hydrate of the cis diastereomer is obtained at a yield of 46% and a purity of greater than 95%. The isomer ratio in the crystal fraction was 99.8% cis isomer to 0.2% trans isomer.

Example 10

20 g of a diastereomeric base mixture of (±)-cis/trans-2-[(dimethylamino)methyl]-1-(3-methoxyphenyl)cyclohexanol (cis:trans isomer ratio=75:25) were dissolved in 20 g of ethanol at 22° C. and combined with 50 vol. % of water. The solution was cooled to 6° C. and left to stand for 6 hours. The resultant crystals were removed by suction filtration and washed twice with 10 ml portions of ethanol/water. After drying, the hydrate of the cis diastereomer is obtained at a yield of 50% and a purity of greater than 95%. The isomer ratio in the crystal fraction was 99.5% cis isomer to 0.5% trans isomer.

Example 11

20 g of a diastereomeric base mixture of (±)-cis/trans-2-[(dimethylamino)methyl]-1-(3-methoxyphenyl)

cyclohexanol (trans:cis isomer ratio=75:25) were dissolved in 20 g of ethanol at 22° C. and combined with 60 vol. % of water. The solution was cooled to 6° C. and left to stand for 6 hours. The resultant crystals were removed by suction filtration and washed twice with 10 ml portions of ethanol/water. After drying, the hydrate of the cis diastereomer is obtained at a yield of 53% and a purity of greater than 95%. The isomer ratio in the crystal fraction was 99.6% cis isomer to 0.4% trans isomer.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A process for separating diastereomeric bases of 2-[(dimethylamino)methyl]-1-(3-methoxyphenyl)cyclohexanol, said process comprising treating a diastereomeric base mixture with a cis:trans isomer ratio of below 80:20 with water in an at least stoichiometric quantity for complete conversion of the bases, and subsequently separating precipitated hydrate of the cis diastereomer.

2. A process according to claim 1, wherein the diastereomeric base mixture has a cis:trans isomer ratio in the range from 60:40 to 75:25.

3. A process according to claim 1, wherein the diastereomeric base mixture is dissolved in a water-miscible organic solvent or mixture of solvents selected from the group consisting of alcohols, ketones, esters, ethers, low molecular weight polyalcohols and aromatic hydrocarbons before the treatment with water.

4. A process according to claim 3, wherein the organic solvent or mixture of solvents is used in a volume ratio to water of 10:2 to 10:5.

5. A process according to claim 3, wherein said organic solvent or mixture of solvents is selected from the group consisting of $C_{1-8}$ alcohols; $C_{3-8}$ ketones; $C_{2-8}$ esters; aliphatic, aromatic, open-chain and cyclic $C_{4-8}$ ethers; $C_{2-6}$ polyalcohols; and $C_{6-9}$ aromatics.

6. A process according to claim 1, further comprising washing separated hydrate crystals of the cis diastereomer with a mixture of at least one water-miscible organic solvent selected from the group consisting of alcohols, ketones, esters, ethers, low molecular weight polyalcohols and aromatic hydrocarbons and water in a volume ratio of 10:2–10:5, and then drying the washed crystals.

* * * * *